United States Patent
Guo et al.

(10) Patent No.: US 11,345,682 B2
(45) Date of Patent: May 31, 2022

(54) POLYMORPH OF HDAC6-SELECTIVE INHIBITOR AND APPLICATION THEREOF

(71) Applicants: CSTONE PHARMACEUTICALS (SUZHOU) CO., LTD., Jiangsu (CN); CSTONE PHARMACEUTICALS (SHANGHAI) CO., LTD., Shanghai (CN); CSTONE PHARMACEUTICALS, Grand Cayman (KY)

(72) Inventors: Qiang Guo, Shanghai (CN); Changqing Wei, Shanghai (CN); Yao Xiao, Shanghai (CN); Lili Fan, Shanghai (CN); Wenyuan Qian, Shanghai (CN)

(73) Assignees: CSTONE PHARMACEUTICALS (SUZHOU) CO., LTD., Jiangsu (CN); CSTONE PHARMACEUTICALS (SHANGHAI) CO., LTD., Shanghai (CN); CSTONE PHARMACEUTICALS, Grand Cayman (KY)

( * ) Notice: Subject to any disclaimer, the term of this patent is extended or adjusted under 35 U.S.C. 154(b) by 0 days.

(21) Appl. No.: 17/256,670

(22) PCT Filed: Jul. 3, 2019

(86) PCT No.: PCT/CN2019/094602
§ 371 (c)(1),
(2) Date: Dec. 29, 2020

(87) PCT Pub. No.: WO2020/007329
PCT Pub. Date: Jan. 9, 2020

(65) Prior Publication Data
US 2021/0147394 A1    May 20, 2021

(30) Foreign Application Priority Data

Jul. 4, 2018 (CN) .......................... 201810726102.X

(51) Int. Cl.
C07D 405/04    (2006.01)
(52) U.S. Cl.
CPC ........ C07D 405/04 (2013.01); C07B 2200/13 (2013.01)
(58) Field of Classification Search
CPC ...................... C07D 405/04; C07B 2200/13
USPC ........................................................ 514/336
See application file for complete search history.

(56) References Cited

U.S. PATENT DOCUMENTS

| 6,627,646 B2 * | 9/2003 | Bakale ................... A61P 37/08 514/322 |
| 9,409,890 B2 | 8/2016 | van Duzer et al. |
| 10,745,389 B2 * | 8/2020 | Wu ...................... A61K 31/435 |
| 2012/0121502 A1 | 5/2012 | van Duzer et al. |
| 2014/0142104 A1 | 5/2014 | van Duzer et al. |
| 2017/0096403 A1 | 4/2017 | van Duzer et al. |

FOREIGN PATENT DOCUMENTS

| CN | 103429574 A | 12/2013 |
| EP | 3569592 A1 | 11/2019 |
| WO | WO-2015007870 A1 | 1/2015 |
| WO | WO-2015100363 A1 | 7/2015 |
| WO | WO-2018130155 A1 | 7/2018 |

OTHER PUBLICATIONS

Golub et al, Science, vol. 286, Oct. 15, 1999, pp. 531-537.*
Glaser, "HDAC Inhibitors: Clinical Update and Mechanism-Based Potential," Biochemical Pharmacology, 2007 74(5), 659-671.*
Pearce et al., Failure modes in anticancer drug discovery and development, Cancer Drug Design and Discovery Edited by Stephen Neidle, Chapter 18, pp. 424-435 (2008).*
Takai et al., "Human Ovarian, etc.," American Cancer Society, 2004; 101(12) 2760-2770.*
Simone, Oncology:Introduction, Cecil Textbook of Medicine, ed Bennett et al. W.B.Saunders CO. 20th ed, vol. 1, 1996, pp. 1004-1010.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Ouaissi et al., "Rationale for Possible, etc.," Journal of Biomedicine and Biotechnology, 2011, Article: ID 315939, 1-8.*
CMU Pharmaceutical polymorphism, internet p. 1-3 (2002) printout Apr. 3, 2008.*
Layzer et al., "Section Five, etc.," Cecil Textbook of Medicine, 20th ed., 2, pp. 2050-2057. (Year: 1996).*
Halebian et al., "Pharmaceutical Applications, etc.," Pharmacuetical Sciences 58(8), 911-929. (Year: 1969).*

(Continued)

Primary Examiner — Nizal S Chandrakumar

(57) ABSTRACT

Disclosed in the present invention are a polymorph A of a compound represented by formula (I), and an application thereof in preparation of drugs for treating HDAC6-associated diseases.

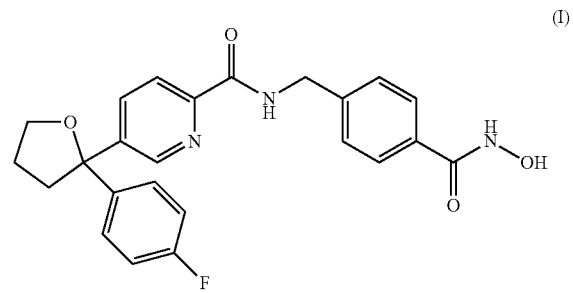

(I)

8 Claims, 2 Drawing Sheets

(56) References Cited

OTHER PUBLICATIONS

Kirk-Othmer Encyclopedia of Chemical Technology, 8, pp. 95-147. (Year: 2002).*
US Pharmacopia #23 National Formulary #18, 1843-1844 (Year: 1995).*
Concise Encyclopedia Chemistry, NY: Walter de Gruyter, 1993, 872-873.*
International Search Report and Written Opinion regarding International Application No. PCT/CN2019/094602, dated Oct. 8, 2019.
Extended European Search Report regarding Application No. 19829797.0, dated Feb. 28, 2022.
Chinese Office Action regarding Application No. 201980044805.7, dated Jan. 30, 2022.

* cited by examiner

POLYMORPH OF HDAC6-SELECTIVE INHIBITOR AND APPLICATION THEREOF

The present disclosure claims the following right of priority:

CROSS-REFERENCE TO RELATED APPLICATIONS

The present application is a National Stage of International Application No. PCT/CN2019/094602, filed on Jul. 3, 2019, which claims priority of the Chinese Patent Application No. CN201810726102.X, filed on Jul. 4, 2018, the contents of which are incorporated herein by reference in their entireties.

TECHNICAL FIELD

The present disclosure relates to a polymorph A of a compound represented by formula (I), and a use thereof in preparation of drugs for treating HDAC6-associated diseases.

BACKGROUND

Experts of WHO predict that the global population will reach 8 billion in 2020, the incidence of cancer will reach 20 million, and the deaths will reach 12 million. Cancer will become the number one killer to humans in the new century and become the most serious threat to human survival. In the process of industrialization, China has become the second most cancer prone country in the world after the United States, and the incidence and mortality of the cancer in China have shown a significant upward trend. Urban cancer is the first cause of death, and rural cancer is the second cause of death. With the rapid increase in the morbidity and mortality of cancer in China, the national annual medical expenses for cancer have exceeded RMB 150 billion.

HDAC inhibitors are widely used in a variety of cancers and can be combined with a variety of drugs to enhance the therapeutic effect of the drugs. HDAC is a fully confirmed anti-tumor target. Histone deacetylase (HDAC) and histone acetyl transferase (HAT) co-regulate gene transcription in the nucleus. In cancer cells, the overexpression of HDAC leads to the enhancement of deacetylation, thereby increasing the attraction between DNA and histones, making the nucleosomes very close, which is not conducive to the expression of tumor suppressor genes. Inhibitors (HDACi) can regulate the expression of cell apoptosis and differentiation-related proteins by increasing histone acetylation to induce cell apoptosis and differentiation, becoming a new class of anti-tumor drugs. Not only that, HDAC is also involved in the regulation of many metabolic diseases, such as Alzheimer, Parkinson and other diseases. HDACi inhibitors have shown good effects in animal and human trials.

Among the 18 subtypes of deacetylase, HDAC6 is the only subtype of deacetylase in the cytoplasm, while the other 17 HDACs are all present in the nucleus. HDAC6 does not directly catalyze histone, but uses tubulin and heat shock protein (Hsp90) as substrates to regulate cell trafficking, adhesion and motility (i.e., no gene regulation). Therefore, it is believed that it will have fewer effects on gene-related physiological functions and thus have fewer side effects. The current clinical trial results have confirmed that HDAC6 selective inhibitors are safe and effective (POC). The clinical study of the first HDAC6 selective inhibitor ACY-1215 (Acetylon) proved that selective HDAC6 inhibitors have better safety and therefore have better business prospects.

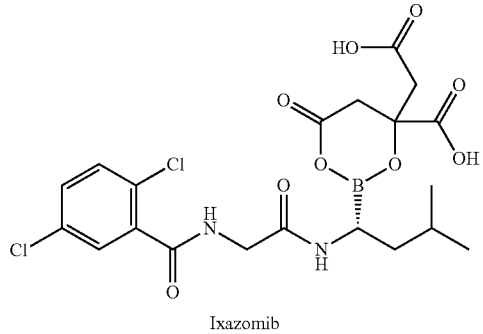 [SMILES: CC(C)C[C@H](NC(=O)CNC(=O)c1cc(Cl)ccc1Cl)B1OC(=O)CC(CC(=O)O)(C(=O)O)O1]

Ixazomib

CONTENT OF THE PRESENT INVENTION

The present disclosure provides a polymorph A of a compound of formula (I), wherein the X-ray powder diffraction pattern thereof has characteristic diffraction peaks at the following 2θ angles: 11.53±0.2°, 18.46±0.2°, and 23.60±0.2°.

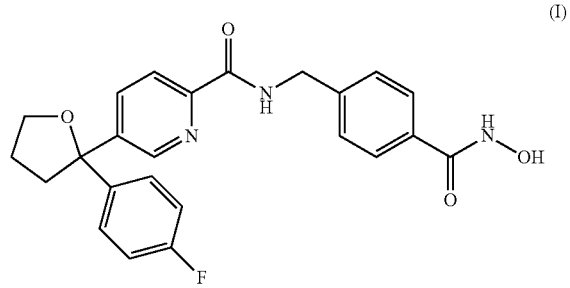 [SMILES: O=C(NO)c1ccc(CNC(=O)c2ccc(C3(c4ccc(F)cc4)CCCO3)cn2)cc1]

(I)

In some embodiments of the present disclosure, the X-ray powder diffraction pattern of the above-mentioned polymorph A has characteristic diffraction peaks at the following 2θ angles: 11.53±0.2°, 13.21±0.2°, 16.33±0.2°, 17.42±0.2°, 18.46±0.2°, 21.43±0.2°, 22.57±0.2°, and 23.60±0.2°.

In some embodiments of the present disclosure, the X-ray powder diffraction pattern of the above-mentioned polymorph A has characteristic diffraction peaks at the following 2θ angles: 8.898°, 11.118°, 11.528°, 12.652°, 13.206°, 13.761°, 16.325°, 17.415°, 18.067°, 18.464°, 19.289°, 20.697°, 21.427°, 22.572°, 23.226°, 23.599°, 25.674°, 26.619°, 27.611°, 29.090°, 29.879°, 31.852°, 33.878°, 35.252°, and 36.122°.

In some embodiments of the present disclosure, the XRPD pattern of the above-mentioned polymorph A is as shown in FIG. 1.

In some embodiments of the present disclosure, the XRPD pattern analysis data of the above-mentioned polymorph A is as shown in Table 1:

TABLE 1

The XRPD pattern analysis data of the polymorph A

| No. | 2θ angle (°) | Interplanar spacing (Å) | Relative intensity (%) |
|---|---|---|---|
| 1 | 8.898 | 9.9297 | 9.7 |
| 2 | 11.118 | 7.9517 | 20.1 |
| 3 | 11.528 | 7.6694 | 47.7 |
| 4 | 12.652 | 6.9909 | 10.7 |
| 5 | 13.206 | 6.6986 | 23.3 |
| 6 | 13.761 | 6.43 | 6.9 |
| 7 | 16.325 | 5.4251 | 25.7 |
| 8 | 17.415 | 5.0879 | 58.4 |
| 9 | 18.067 | 4.9058 | 95.1 |
| 10 | 18.464 | 4.8013 | 100 |
| 11 | 19.289 | 4.5977 | 6.4 |
| 12 | 20.697 | 4.288 | 20.8 |
| 13 | 21.427 | 4.1435 | 35.2 |
| 14 | 22.572 | 3.9359 | 91.3 |
| 15 | 23.226 | 3.8266 | 14.3 |
| 16 | 23.599 | 3.7668 | 24.4 |
| 17 | 25.674 | 3.467 | 9.5 |
| 18 | 26.619 | 3.3459 | 17.7 |
| 19 | 27.611 | 3.2279 | 12.8 |
| 20 | 29.09 | 3.0671 | 19.2 |
| 21 | 29.879 | 2.9879 | 6.6 |
| 22 | 31.852 | 2.8072 | 5.2 |
| 23 | 33.878 | 2.6438 | 7.2 |
| 24 | 35.252 | 2.5439 | 6.6 |
| 25 | 36.122 | 2.4845 | 6.8 |

In some embodiments of the present disclosure, the differential scanning calorimeter curve of the above-mentioned polymorph A has an endothermic peak with an onset at 135.55° C.

In some embodiments of the present disclosure, the DSC pattern of the above-mentioned polymorph A is as shown in FIG. 2.

In some embodiments of the present disclosure, the thermogravimetric analysis curve of the above-mentioned polymorph A shows a weight loss of 0.2115% at 135.40° C.±3° C.

In some embodiments of the present disclosure, the TGA pattern of the above-mentioned polymorph A is as shown in FIG. 3.

The present disclosure also provides use of the above-mentioned polymorph A in the manufacture of drugs for treating HDAC6-associated diseases.

TECHNICAL EFFECTS

The polymorph A of the compound of formula (I) in the present disclosure is stable, less affected by light, heat and humidity, and has good efficacy in vivo, and has a broad prospect for preparation of drugs.

Definition and Description

Unless otherwise stated, the following terms and phrases used herein are intended to have the following meanings. A specific phrase or term should not be considered uncertain or unclear unless specifically defined, but should be understood in an ordinary meaning. When a trade name appears herein, it is intended to refer to the corresponding commodity or an active ingredient thereof.

The intermediate compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The chemical reactions described in the specific embodiments of the present disclosure are completed in a suitable solvent, wherein the solvent must be suitable for the chemical changes of the present disclosure and the reagents and materials required thereby. In order to obtain the compounds of the present disclosure, sometimes a person skilled in the art needs to modify or select synthesis steps or reaction schemes based on the existing embodiments.

The present disclosure will be specifically described below by way of examples which are not intended to limit the present disclosure in any way.

All solvents used in the present disclosure are commercially available and can be used without further purification.

The solvents used in the present disclosure are commercially available. The present disclosure uses the following abbreviations: EtOH represents ethanol; MeOH represents methanol; TFA represents trifluoroacetic acid; TsOH represents p-toluenesulfonic acid; mp represents melting point; $EtSO_3H$ represents ethanesulfonic acid; $MeSO_3H$ represents methanesulfonic acid; THF represents tetrahydrofuran; EtOAc represents ethyl acetate.

The X-Ray Powder Diffractometer (XRPD) Method in the Present Disclosure

Instrument model: Bruker D8 advance X-ray diffractometer

Test method: approximately 10 mg to 20 mg of the sample is used for XRPD detection.

The detailed XRPD parameters are as follows:

Light tube: Cu, kα, (λ=1.54056 Å).
Light tube voltage: 40 kV, light tube current: 40 mA
Divergence slit: 0.60 mm
Detector slit: 10.50 mm
Anti-scatter slit: 7.10 mm
Scanning range: 4-40 deg
Step size: 0.02 deg
Step length: 0.12 sec
Sample disk rotating speed: 15 rpm The Differential Scanning Calorimeter (DSC) Method in the Present Disclosure Instrument model: TA Q2000 differential scanning calorimeter Test method: The sample (about 1 mg) was placed in a DSC aluminum pan for testing. The sample was heated from 30° C. (room temperature) to 300° C. (or 350° C.) at a heating rate of 10° C./min under the condition of 50 mL/min of $N_2$.

The Thermal Gravimetric Analyzer (TGA) Method in the Present Disclosure

Instrument model: TA Q5000IR thermal gravimetric analyzer

Test method: The sample was placed (2 mg to 5 mg) in a TGA platinum pan for testing. The sample was heated from room temperature to 350° C. or to 20% of weight loss at a heating rate of 10° C./min under the condition of 25 mL/min $N_2$.

DETAILED DESCRIPTION OF THE PREFERRED EMBODIMENT

Figure 1:
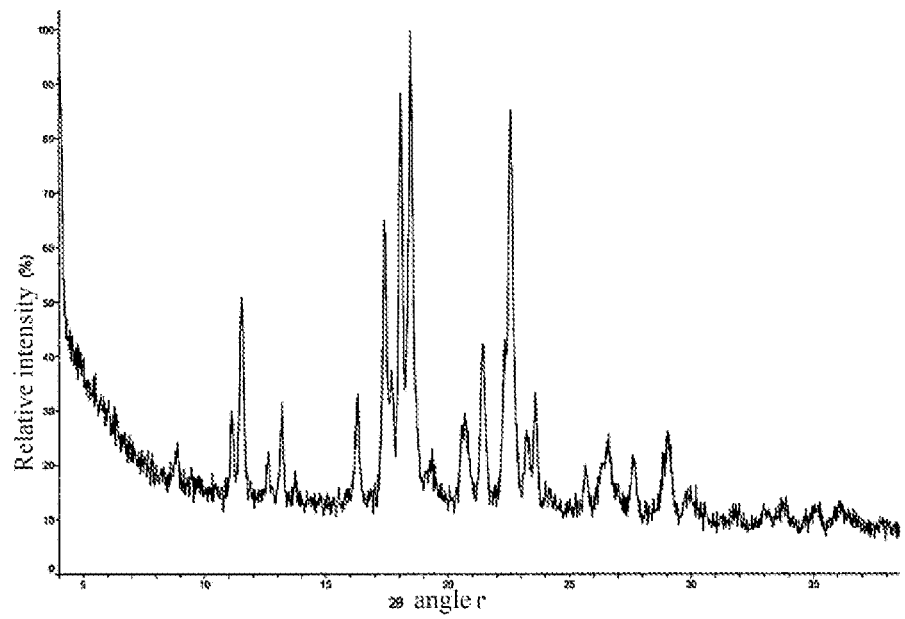
FIG. 1 is an XRPD pattern of Cu-Kα radiation of the polymorph A of the compound of formula (I)

In order to better understand the content of the present disclosure, the following specific examples are used for further description, but the specific embodiments do not limit the content of the present disclosure.

Example 1: Preparation of a Compound of Formula (I)

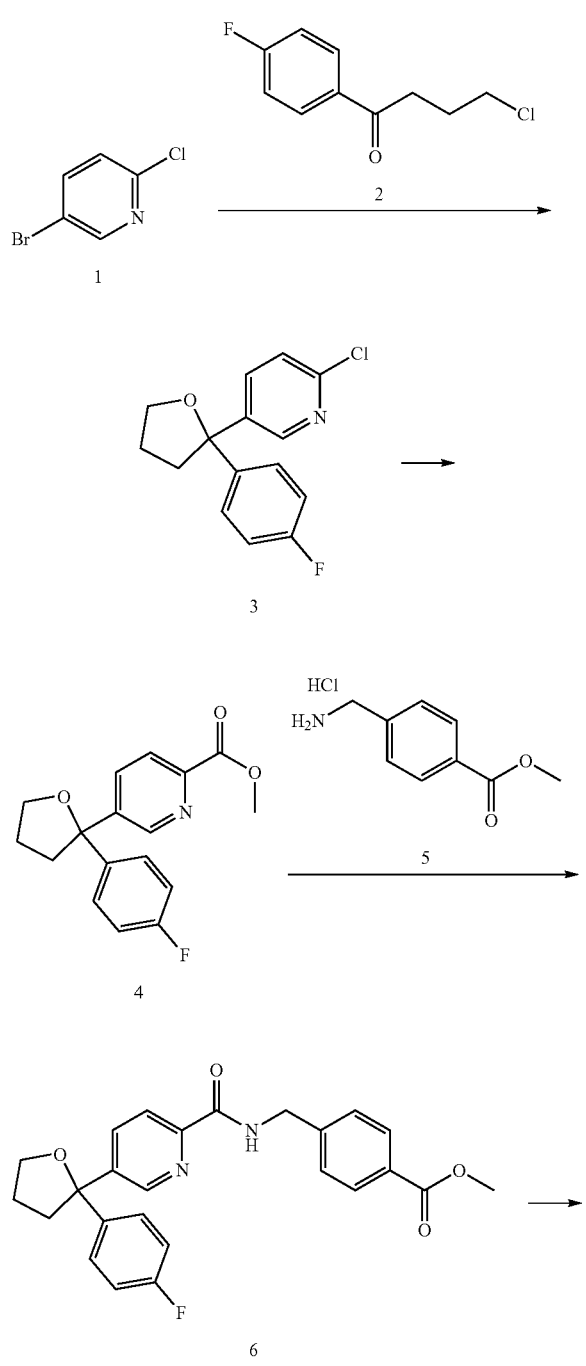

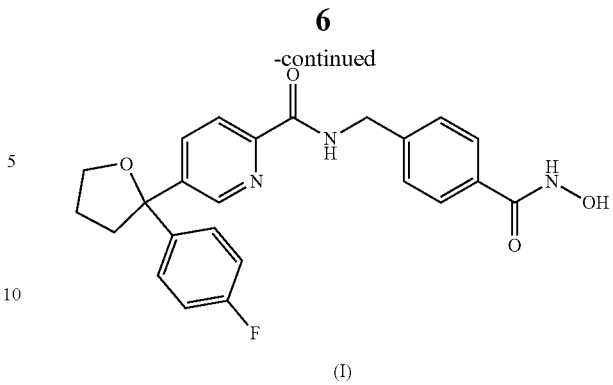

(I)

Step 1:

Under $N_2$ protection, compound 1 (1.712 kg, 8.90 mol, 1.0 equivalent) and toluene (17 L) were added successively into a reaction kettle, and the temperature in the kettle was adjusted to −70° C. with a dry ice ethanol bath. A solution of 2.5 M n-butyl lithium (3.92 L, 9.79 mol, 1.1 equivalents) in n-heptane was added dropwise into the reaction kettle with a peristaltic pump, and the dropping rate was controlled so that the temperature in the kettle was not higher than −70° C. After the dropwise addition was complete, the reaction solution was stirred continuously at this temperature for 1 hour. A prepared solution of compound 2 (1.785 kg, 8.90 mol, 1.0 equivalent) in toluene (1.8 L) was added into the above-mentioned system with a peristaltic pump, and the addition rate was controlled so that the temperature in the kettle was not higher than −50° C. Then the dry ice ethanol bath was removed to raise the reaction system to 15° C. to 20° C., and the reaction solution was stirred continuously for 14 hours. After the reaction monitored by HPLC was complete, saturated aqueous ammonium chloride solution (2 L) and water (10 L) were added successively, the organic phase was separated, and the aqueous phase was extracted with ethyl acetate (3 L×2). The combined organic phase was dried over anhydrous sodium sulfate and filtered, and the filtrate was concentrated to dryness under reduced pressure. The resulting brown-black oil was filtered with silica gel (n-heptane: ethyl acetate was at a ratio of 5:1), and the filtrate was concentrated under reduced pressure to dryness to obtain compound 3. $^1$H NMR (400 MHz, CDCl$_3$): δ 8.26-8.35 (m, 1H), 7.50-7.60 (m, 1H), 7.20-7.30 (m, 2H), 7.13 (d, J=8.0 Hz, 1H), 6.80-6.95 (m, 2H), 3.94 (t, J=6.8 Hz, 2H), 2.36-2.55 (m, 2H), 1.80-1.93 (m, 2H); MS ESI calculated value $C_{15}H_{13}ClFNO$ [M+H]+278, measured value 278.

Step 2:

Compound 3 (0.6 kg, 2.16 mol, 1.0 equivalent), palladium acetate (0.022 kg, 0.098 mol, 0.05 equivalent), triethylamine (0.6 L, 4.32 mol, 2.0 equivalent), 1,3-bisdiphenylphosphine propane (0.089 kg, 0.216 mol, 0.1 equivalent) and methanol (6 L) were added successively to a 10 L autoclave reaction kettle, and the resulting mixture was replaced with argon three times, introduced with 2 MPa of carbon monoxide gas, and heated to 100° C. to 105° C. and stirred for 24 hours. The reaction was carried out four times in parallel. The reaction solutions were combined and then post-processed. The combined reaction solution was filtered, and the filtrate was concentrated to dryness under reduced pressure. Then ethyl acetate (10 L) and water (5 L) were added successively, and the resulting mixture was stirred and left to stand to separate the organic phase, and the aqueous phase was extracted with ethyl acetate (2 L×2). The combined organic phase was dried over anhydrous sodium sulfate and filtered, and the filtrate was concentrated to dryness under reduced pressure. Then the resulting product was filtered with silica gel (dichloromethane:ethyl acetate was at a ratio of 5:1), and the filtrate was concentrated to dryness under reduced pressure to obtain 2.15 kg of crude product. The solid was dissolved in ethyl acetate (21 L) and activated carbon (430 g) was added and refluxed for 12 hours. The resulting product was filtered through Celite while it was hot, and the filter cake was rinsed with hot ethyl acetate (2 L×2). The combined filtrate was concentrated to dryness under reduced pressure to obtain compound 4. $^1$H NMR (400 MHz, CDCl3) δ: 8.79 (d, J=1.6 Hz, 1H), 8.05 (d, J=8.4 Hz, 1H), 7.85 (dd, J=8.0, 1.6 Hz, 1H), 7.30-7.45 (m, 2H), 6.90-7.05 (m, 2H), 4.00-4.10 (m, 2H), 3.98 (s, 3H), 2.43-2.70 (m, 2H), 1.85-2.05 (m, 2H); MS ESI calculated value $C_{17}H_{16}FNO_3$ [M+H]+302, measured value 302.

Step 3:

Under nitrogen purge, to a 5 L three-necked flask with a solution of compound 4 (0.2 kg, 0.664 mol, 1.0 equivalent) and compound 5 (0.134 kg, 0.664 mol, 1.0 equivalent) in tetrahydrofuran (2 L) was added dropwise 2 M trimethylaluminum toluene solution (0.66 L, 1.32 mol, 2.0 equivalents) at room temperature, and the dropping rate was controlled so that the internal temperature was not higher than 50° C. After the dropwise addition was completed, the system was heated and stirred at 70° C. for 20 minutes. After the reaction was complete, the reaction solution was concentrated to dryness under reduced pressure. The resulting brown-black viscous paste was quenched with 2 M aqueous sodium hydroxide solution at 0° C. under nitrogen purge, until it turned into a yellow-brown solid. The reaction and quenching process were carried out in parallel ten times and then combined. To the yellow-brown solid obtained above was added a mixed solution of dichloromethane and methanol (a volume ratio of 10:1, 20 L), and added dropwise 2 M sodium hydroxide aqueous solution with constant stirring until the suspension turned into a gel jelly. At this time, anhydrous sodium sulfate (5 kg) was add to the system and stirred continuously. The above-mentioned solid-liquid mixture was filtered through Celite, and the filtrate was collected, stirred repeatedly with a mixed solution of dichloromethane and methanol (a volume ratio of 10:1, 5 L×4) and filtered, and the combined filtrate was concentrated to dryness under reduced pressure. The crude product was purified by silica gel column chromatography (n-heptane:ethyl acetate:dichloromethane was at a ratio of 3:1:1) to obtain compound 6. $^1$H NMR (400 MHz, CDCl$_3$) δ: 8.59 (s, 1H), 8.38 (brs, 1H), 8.15 (d, J=8.0 Hz, 1H), 8.00 (d, J=8.4 Hz, 2H), 8.70-8.90 (m, 1H), 7.37-7.45 (m, 4H), 6.94-7.05 (m, 2H), 4.71 (d, J=6.4 Hz, 2H), 4.07 (t, J=7.2 Hz, 2H), 3.91 (s, 3H), 2.45-2.65 (m, 2H), 1.90-2.05 (m, 2H); MS ESI calculated value $C_{25}H_{23}FN_2O_4$ [M+H]+435, measured value 435.

Step 4:

In a 50 L reaction kettle, to a solution of compound 6 (2.1 kg, 4.83 mol, 1.0 equivalent) in dichloromethane (4 L) and methanol (20 L) was added 50% hydroxylamine aqueous solution (8 L) at 0° C. When the internal temperature was 0° C., 2 M sodium hydroxide aqueous solution (3 L) was started to be added dropwise and the internal temperature was remained at this temperature. After the dropwise addition was complete, the reaction solution was slowly raised to 6° C. to 13° C. and stirred continuously for 12 hours. After the reaction was complete, most of the organic solvent was removed under reduced pressure. Ice water was added to cool the internal temperature to 0° C., and concentrated hydrochloric acid was added to adjust the pH to a range of 7 to 8 under constant stirring. The precipitated white solid was filtered and rinsed with water (2 L×3). The resulting solid was dispersed in ethyl acetate (21 L) and water (10.5 L), and the pH was adjusted to 2-3 with concentrated hydrochloric acid under constant stirring. At this time, the white solid was dissolved in the organic phase, and the organic phase was separated. The aqueous phase was extracted with ethyl acetate (5 L×2), and the combined organic phase was washed with brine, dried over anhydrous sodium sulfate and filtered, and the filtrate was concentrated to dryness under reduced pressure to obtain the compound of formula (I). $^1$H NMR (400 MHz, CDCl$_3$) δ: 11.15 (brs, 1H), 10.22 (brs, 1H), 9.35 (t, J=6.4 Hz, 1H), 8.72 (d, J=1.5 Hz, 1H), 8.01-8.07 (m, 1H), 7.94-8.00 (m, 1H), 7.68 (d, J=8.3 Hz, 2H), 7.49-7.56 (m, 2H), 7.34 (d, J=8.3 Hz, 2H), 7.15 (t, J=8.9 Hz, 2H), 4.51 (d, J=6.3 Hz, 2H), 3.98 (t, J=7.2 Hz, 2H), 2.62 (t, J=7.2 Hz, 2H), 1.89 (qd, J=7.2, 5.1 Hz, 2H); MS ESI calculated value $C_{24}H_{22}FN_3O_4$ [M+H]+436, measured value 436.

Example 2: Preparation of Polymorph a of the Compound of Formula (I)

The compound of formula (I) (0.21 kg) was stirred with EtOAc (2.1 L) and water (1 L), and concentrated hydrochloric acid (8 mL) was added to dissolve the solid in the organic phase. The organic phase was separated, washed with brine (0.5 L, the pH of the brine was about 6 after washing), dried over anhydrous sodium sulfate and filtered, and the filtrate was concentrated to dryness under reduced pressure to obtain a foamy white solid. To the solid was added preheated ethyl acetate (2.1 L) to keep the internal temperature at 45° C., and n-heptane (0.588 L) was started to be added dropwise. After the dropwise addition was complete, the internal temperature was slowly cooled to 6° C. to 13° C., and the mixture was stirred continuously for 12 hours. The resulting mixture was filtered, and the filter cake was collected to obtain the first recrystallization product. The process was carried out 10 times in parallel, and a total of 1.5 kg of white solid product was obtained.

The first recrystallization product (0.25 kg) was stirred with EtOAc (2.5 L) and water (1.25 L), and concentrated hydrochloric acid (about 80 mL) was added to dissolve the solid in the organic phase. The organic phase was separated, washed with water (0.6 L×2) and brine (0.6 L, the pH of the brine was about 6 after washing), dried over anhydrous sodium sulfate and filtered, and the filtrate was concentrated to dryness under reduced pressure to obtain a foamy white solid. To the solid was added preheated ethyl acetate (2.5 L) to keep the internal temperature at 45° C., and n-heptane (0.7 L) was started to be added dropwise. After the dropwise addition was complete, the internal temperature was slowly cooled to 6° C. to 13° C. and the mixture was stirred continuously for 12 hours. The resulting mixture was filtered, and the filter cake was collected to obtain the second recrystallization product. The process was carried out 6 times in parallel, and a total of 1.05 kg of product (white solid) was obtained.

The second recrystallized product (1.05 kg) was stirred with EtOAc (0.7 L) and water (1.4 L) at 5° C. for 24 hours. The resulting mixture was filtered, and the filter cake was rinsed with water (105 mL×2), drained, and then dried in a vacuum drying oven with phosphorus pentoxide on the bottom layer at 30° C. for 24 hours to obtain a white solid. The polymorph state thereof was detected by XRPD, and then the polymorph A of the compound of formula (I) was obtained.

Example 3: Solid Stability Test of the Polymorph A of the Compound of Formula (I)

According to the "Guidelines for the Stability Test of Active Pharmaceutical Ingredients and Preparations" (Chinese Pharmacopoeia, 2015, Part IV, General Chapter 9001), the stability of the polymorph A of the compound of formula (I) was investigated under the conditions of high temperature (60° C., open), high humidity (room temperature/relative humidity of 92.5%, open), high temperature and high humidity (40° C., 75% RH; 60° C., 75% RH) and strong light (total illumination of $1.2 \times 10^6$ Lux·hr/near ultraviolet 200 w·hr/m$^2$, sealed).

15 mg of the polymorph A of the compound of formula (I) was weighed, placed on the bottom of a glass sample bottle, and spread into a thin layer. The sample placed under high temperature and high humidity was sealed with aluminum foil paper, and some small holes were pierced in the aluminum foil paper to ensure that the sample can fully contact with the ambient air; The samples placed under strong light conditions were sealed with screw caps. The samples placed under different conditions were sampled and tested (XRPD) on day 5 and day 10. The test results were compared with the initial test results on day 0. The test results are shown in Table 2 below:

TABLE 2

Results of solid stability test of the polymorph A of the compound of formula (I)

| Test conditions | Time point | Polymorph |
|---|---|---|
| — | Day 0 | Polymorph A |
| High temperature (60° C., open) | Day 5 | Polymorph A |
| | Day 10 | Polymorph A |
| High humidity (room temperature/relative humidity of 92.5%, open) | Day 5 | Polymorph A |
| | Day 10 | Polymorph A |
| High temperature and high humidity (40° C., 75% RH; 60° C., 75% RH) | Day 10 1 month | Polymorph A Polymorph A |
| Strong light (5000 1x, sealed) | Day 5 | Polymorph A |
| | Day 10 | Polymorph A |

Conclusion: The polymorph A of the compound of formula (I) has good stability under the conditions of high temperature, high humidity, high temperature and high humidity, and strong light.

Experimental Example 1: In Vivo Pharmacodynamic Study of the Polymorph A of the Compound of Formula (I) in MM.1S Xenograft (CDX) Model Experimental Materials:

CB-17 SCID mice, female, 6 weeks to 8 weeks old, weight of about 17 grams to 20 grams. The mice were kept in a special pathogen-free environment and in a single ventilated cage (4 mice per cage). All cages, bedding and water were disinfected before use. All animals had free access to standard certified commercial laboratory food. A total of 64 mice purchased from Beijing Vital River Co., Ltd. were used for study. 0.2 mL of $5 \times 10^6$ MM.1S cells were subcutaneously inoculated on the right back of each mouse for tumor growth. The experiment was performed when the average tumor volume reached about 100 cubic millimeters to 150 cubic millimeters.

Experimental Method:

In vivo selective experiments were performed on CB-17 SCID mice implanted subcutaneously with human multiple myeloma cells MM.1S xenograft (CDX). The polymorph A of the compound of formula (I) was formulated with a mixed solution of 5% of dimethyl sulfoxide and 95% of 10% hydroxypropyl-β-cyclodextrin into a formulation to be administered orally for 5 days and stopped for 2 days. Ixazomib was administered once on the first day and fourth day of each week, respectively. The tumor volume was measured with a two-dimensional caliper twice a week, and the volume was measured in cubic millimeters and calculated by the following formula: $V=0.5\ a*b^2$, in which a and b were the long diameter and short diameter of the tumor, respectively. The anti-tumor efficacy was determined by dividing the average tumor increase volume of animals treated with the compound by the average tumor increase volume of untreated animals.

Experimental Results: See Table 3.

TABLE 3

Results of in vivo efficacy study

| | Tumor volume (mm$^3$) | | | | | | |
|---|---|---|---|---|---|---|---|
| Test compounds | Day 0 | Day 3 | Day 5 | Day 7 | Day 10 | Day 12 | Day 14 |
| Blank group | 134 | 215 | 413 | 639 | 1065 | 1598 | 2046 |
| Ixazomib (4 mg/kg, twice a week) | 134 | 157 | 193 | 331 | 634 | 835 | 1257 |
| Polymorph A of the compound of formula (I) (75 mg/kg, administration for 5 days and drug withdrawal for 2 days) | 134 | 165 | 319 | 466 | 753 | 1006 | 1532 |
| Polymorph A of the compound of formula (I) (15 mg/kg, administration for 5 days and drug withdrawal for 2 days) + ixazomib (4 mg/kg, twice a week) | 134 | 151 | 225 | 322 | 501 | 771 | 1240 |
| Polymorph A of the compound of formula (I) (30 mg/kg, administration for 5 days | 134 | 117 | 149 | 183 | 341 | 437 | 644 |

TABLE 3-continued

Results of in vivo efficacy study

| Test compounds | Tumor volume (mm³) | | | | | | |
|---|---|---|---|---|---|---|---|
| | Day 0 | Day 3 | Day 5 | Day 7 | Day 10 | Day 12 | Day 14 |
| and drug withdrawal for 2 days) + ixazomib (4 mg/kg, twice a week) | | | | | | | |
| Polymorph A of the compound of formula (I) (75 mg/kg, administration for 5 days and drug withdrawal for 2 days) + ixazomib (4 mg/kg, twice a week) | 134 | 121 | 169 | 231 | 336 | 457 | 720 |

Experiment Conclusion:

The combined administration group of the polymorph A of the compound of formula (I) (75 mg/kg) and ixazomib (4 mg/kg) has a very good combined administration efficacy compared with the blank group, single-use group of the polymorph A of the compound of formula (I) (75 mg/kg) and single-use group of ixazomib (4 mg/kg), and the mice show good tolerance.

What is claimed is:

1. A polymorph A of a compound of formula (I), wherein the X-ray powder diffraction pattern thereof has characteristic diffraction peaks at the following 2θ angles: 11.53±0.2°, 18.46±0.2°, and 23.60±0.2°

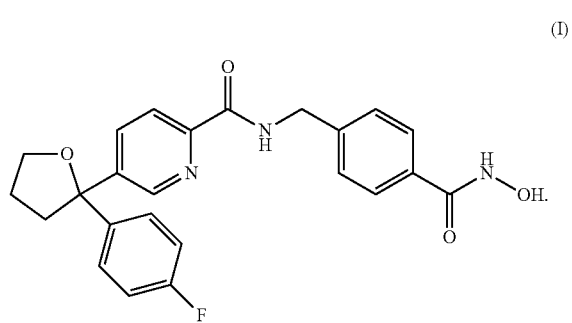 [SMILES: O=C(NO)c1ccc(CNC(=O)c2ccc(C3(c4ccc(F)cc4)CCCO3)cn2)cc1]

(I)

2. The polymorph A as defined in claim 1, wherein the X-ray powder diffraction pattern thereof has characteristic diffraction peaks at the following 2θ angles: 11.53±0.2°, 13.21±0.2°, 16.33±0.2°, 17.42±0.2°, 18.46±0.2°, 21.43±0.2°, 22.57±0.2°, and 23.60±0.2°.

3. The polymorph A as defined in claim 2, wherein the X-ray powder diffraction pattern thereof has characteristic diffraction peaks at the following 2θ angles: 8.898°, 11.118°, 11.528°, 12.652°, 13.206°, 13.761°, 16.325°, 17.415°, 18.067°, 18.464°, 19.289°, 20.697°, 21.427°, 22.572°, 23.226°, 23.599°, 25.674°, 26.619°, 27.611°, 29.090°, 29.879°, 31.852°, 33.878°, 35.252°, and 36.122°.

4. The polymorph A as defined in claim 3, wherein the XRPD pattern thereof is as shown in FIG. 1.

5. The polymorph A as defined in claim 1, wherein the differential scanning calorimeter curve thereof has an endothermic peak with an onset at 135.55° C.

Figure 2:
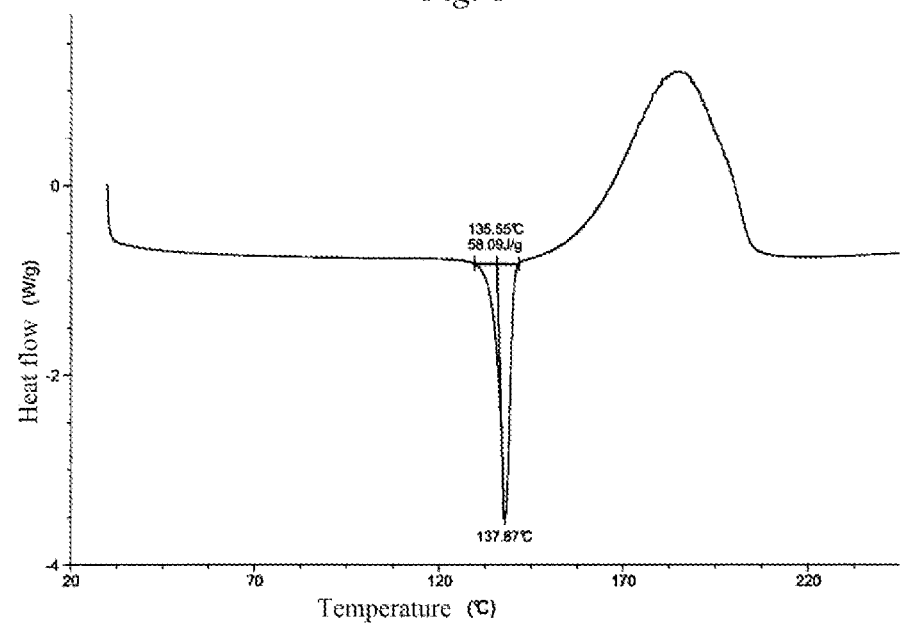
FIG. 2 is a DSC pattern of the polymorph A of the compound of formula (I)

6. The polymorph A as defined in claim 5, wherein the DSC pattern thereof is as shown in FIG. 2.

7. The polymorph A as defined in claim 1, wherein the thermogravimetric analysis curve thereof shows a weight loss of 0.2115% at 135.40° C.±3° C.

Figure 3:
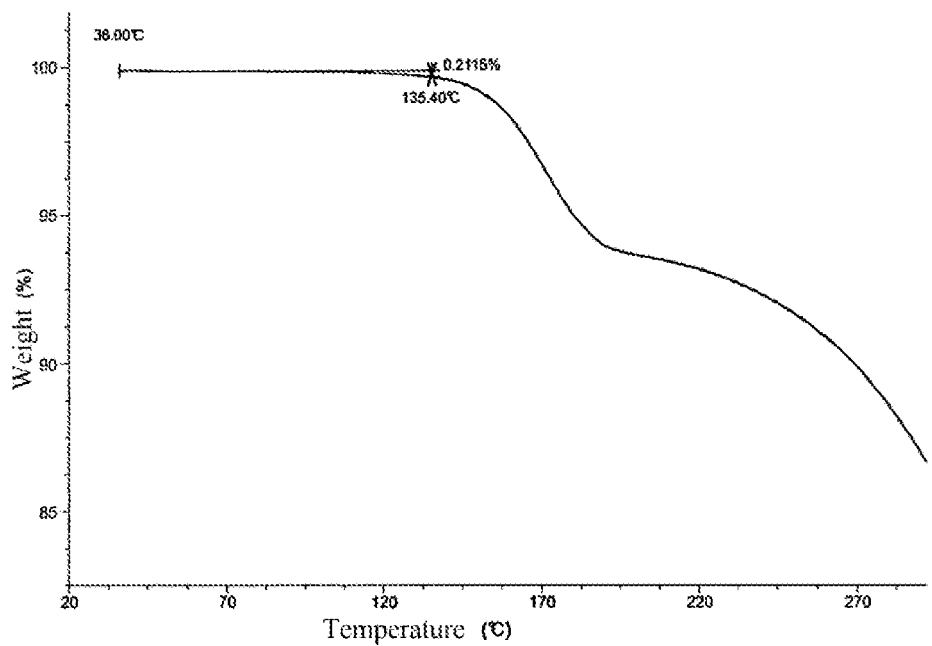
FIG. 3 is a TGA pattern of the polymorph A of the compound of formula (I).

8. The polymorph A as defined in claim 7, wherein the TGA pattern thereof is as shown in FIG. 3.

* * * * *